United States Patent [19]
Guilak

[11] Patent Number: 5,657,398
[45] Date of Patent: Aug. 12, 1997

[54] HIGH-QUALITY, LOW-BIT-RATE METHOD OF COMPRESSING WAVEFORM DATA

[75] Inventor: Farzin G. Guilak, Beaverton, Oreg.

[73] Assignee: Protocol Systems, Inc., Beaverton, Oreg.

[21] Appl. No.: 438,041

[22] Filed: May 8, 1995

Related U.S. Application Data

[63] Continuation of Ser. No. 967,747, Oct. 28, 1992, abandoned.
[51] Int. Cl.$^6$ .................................. G06K 9/36; G06K 9/46
[52] U.S. Cl. ........................... 382/232; 382/128; 128/704
[58] Field of Search .................................. 382/232, 238, 382/100, 128; 364/413.05, 413.06, 715.02; 128/696, 702, 703, 704

[56] References Cited

U.S. PATENT DOCUMENTS

| | | | |
|---|---|---|---|
| 4,314,105 | 2/1982 | Mozer | 179/15.55 R |
| 4,396,906 | 8/1983 | Weaver | 340/347 |
| 4,449,536 | 5/1984 | Weaver | 128/696 |
| 4,503,510 | 3/1985 | Weaver | 364/715 |
| 4,546,342 | 10/1985 | Weaver et al. | 340/347 |
| 4,567,883 | 2/1986 | Langer et al. | 128/696 |
| 4,583,553 | 4/1986 | Shah et al. | 128/704 |
| 4,721,114 | 1/1988 | DuFault et al. | 128/696 |
| 4,732,158 | 3/1988 | Sadeh | 364/413.06 |
| 4,802,222 | 1/1989 | Weaver | 128/696 |
| 4,882,754 | 11/1989 | Weaver et al. | 128/696 |
| 4,920,489 | 4/1990 | Hubelbank et al. | 364/413.06 |
| 4,947,858 | 8/1990 | Smith | 128/696 |

OTHER PUBLICATIONS

A New Data-Reduction Algorithm for Real-Time ECG Analysis, IEEE Transactions on Biomedical Engineering, vol. BME-29, No. 1, Jan. 1982.
Data Compression for Storage of Resting ECGs Digitized at 500 Samples/Second, Biomedical Instrumentation & Technology, pp. 133–149, Mar./Apr. 1992.
Comp.log.edit, May 29, 1992, pp. 1 through 21.
Compression of the Ambulatory ECG by Average Beat Subtraction . . . , IEEE Transactions on Biomedical Engineering, vol. 38, No. 3, Mar. 1991.
An Algorithm for ECG Data Compession Using Spline Functions, IEEE, pp. 575–578, 1987.
ECG Data Compression for Tapeless Ambulatory Monitors, IEEE, pp. 467–470, 1988.

*Primary Examiner*—Leo Boudreau
*Assistant Examiner*—Phuoc Tran
*Attorney, Agent, or Firm*—Kolisch Hartwell Dickinson McCormack & Heuser

[57] ABSTRACT

A high-quality, low-bit-rate method of compressing physiological-waveform data obtained from a signal sent from a diagnostic medical device is disclosed. Associated with the signal are time and voltage characteristics. The method includes the steps of (1) examining such signal during a periodic event in which such data occurs, and which data includes a first region dominated by high-frequency information and a second region dominated by low-frequency information, and (2) removing the first region from the event based upon preselected criteria, which criteria are independent of indicia related to the first region. Also included is the step of compressing the data by processing the removed first region according to a first preselected plan which emphasizes low-bit-rate compression, and by processing the data of the entire event according to a second preselected plan which emphasizes high-quality compression. The removing step may further include the substeps of identifying a set of potential plural peaks associated with the first region, and confirming that the potential peaks are the desired ones by using a preselected frequency analysis.

8 Claims, 2 Drawing Sheets

HIGH-QUALITY, LOW-BIT-RATE METHOD OF COMPRESSING WAVEFORM DATA

This is a continuation of application Ser. No. 07/967,747 filed Oct. 28, 1992, abandoned.

BACKGROUND OF THE INVENTION

The present invention relates to methods of compressing waveform data and more particularly, to a high-quality, low-bit-rate method of compressing such data.

It is known to perform data-compression schemes on measured data as a way of converting that data to a condition for storing it more efficiently than if it were uncompressed. The usual scenario is to design such a scheme that allows the data to be compressed for storage, and then later, as desired, to be uncompressed for use/evaluation of it.

A problem encountered when developing such a scheme is to design it in such a way that it will meet two competing goals: (1) to store the data efficiently, and (2) to store the data in a high-quality format that accommodates substantial representation of the data when it is uncompressed for later use/evaluation.

One setting where such compression schemes are useful is in connection with testing equipment that measures a periodic quantity that changes over time. Commonly, the periodic quantity is measurable via a signal which carries information representative of the quantity. Also, the periodic quantity may be associated with animate or inanimate objects.

In one example, the object is a living subject with a heart and circulatory system, and the periodic quantity is ECG-waveform data associated with that subject, i.e. the periodic electric potentials caused by heart action and occurring between different parts of the body.

Shifting from the example back to the above-referenced general setting, waveform data corresponding to the periodic quantity is obtained by plotting the instantaneous values of the periodic quantity against time. The resulting waveform data provides valuable information, and one such value is that it can be used to provide diagnostic information about the object to which it relates. Again shifting to the above example, ECG-waveform data provides information that is useful to diagnose heart disease.

In applications where waveform data is obtained electronically and where a substantial amount of such data is produced, it becomes necessary to store the data for later retrieval and use/evaluation. Again turning to the example, ECG-waveform data is commonly obtained electronically, stored in memory, and then subsequently retrieved from memory for diagnostic evaluation by health professionals.

There is a need to develop waveform-compression methods to increase waveform-data-storage efficiency and effective transmission bandwidth (the latter relating especially to bidirectionally sending such data using a communication system). In the hospital-ECG-monitoring field it is now common for remote ECG monitors to be connected to patients in their hospital rooms, and to be connected electronically to a central station monitor. There is a specific need associated with this particular application for compressing ECG-waveform data for later retrieval/use because health professionals desire to have what is known as full-disclosure archiving of such data. Full-disclosure archiving involves storing for each patient ECG-waveform data obtained in a 24-hour period.

Consistent with the need for improved data-storage efficiency, there have been many proposals for compressing waveform data. However, none of the conventional proposals has been wholly satisfactory in meeting the competing goals of (1) high compression of waveform data and (2) high quality appearance associated with a waveform reconstructed (i.e. uncompressed) from such compressed data.

Many conventional proposals are also limited because they are based on, and require identification of beats, i.e. the occurrence of a QRS complex which relates to the moment when the ventricles of the heart depolarize and the heart pumps blood through the body. Such beat-based methods require detection of each successive beat, which detection is itself complicated and potentially artifact-producing.

Accordingly, it is a principal object of the present invention to provide a waveform-data-compression method that overcomes the drawbacks of conventional methods.

Another object is to provide such a method that effects waveform-data-compression without requiring beat detection.

A still further object is to provide such method that offers increased waveform-data storage efficiency.

Yet another object is to provide such a method that provides increased effective transmission bandwidth for waveform data.

A still further object is to provide such a method that retains a desired appearance in a waveform reconstructed from a compressed version of it.

SUMMARY OF THE INVENTION

The invention achieves the above objects by providing a high-quality, low-bit-rate method of compressing waveform data obtained from a signal. One step in the method involves examining the signal during a periodic event in which such data occurs, and which data includes a first region dominated by high-frequency information and a second region dominated by low-frequency information. The method also includes the additional steps of (1) removing the first region from the event based upon preselected criteria, which criteria are independent of indicia related to the first region, and (2) compressing the data by processing the removed first region according to a first preselected plan which emphasizes low-bit-rate compression, and by processing the data of the entire event according to a second preselected plan which emphasizes high-quality compression.

The removing step of the method also includes identifying a possible first set of peaks, and confirming that the possible first set is the desired one by using a preselected frequency analysis.

In its preferred embodiment, the present invention is practiced by compressing ECG-waveform data that is generated in a signal from an electronic-vital-signs monitor. The invention is especially useful for archiving ECG data in the memory of a central station in which data is received from remote vital signs monitors positioned in patients' rooms on a hospital floor.

The invention involves compressing an ECG waveform by isolating its high-and low-frequency regions. Each region is then compressed by novel, preselected plans, with a first preselected plan emphasizing low-bit-rate compression of the high-frequency regions. A second, preselected plan emphasizes high-quality compression of the entire waveform. The resulting, compressed waveform is represented by an optimum number of bits, which number is sufficiently low for compression purposes and yet effective to maintain the clinical appearance of the waveform when the latter is reconstructed by uncompressing the data and displaying/printing it.

A key feature of the invention is that it is not dependent on knowledge of prior beat locations. This feature is obtained by using and applying a so-called recursive partitioning algorithm (RPA). RPA's are known generally for use in waveform compression schemes, but no one has proposed using them to isolate high-frequency components of a waveform as part of the above-described method.

The advantages offered by the invention include (1) increased storage efficiency, (2) increased effective transmission bandwidth and (3) retention of clinical appearance in reconstructed waveform from compressed version of it. The latter advantage is what is referred to herein as high-quality compression of such waveform data. In other words, the high-quality compression of ECG-waveform data that is obtainable by practicing the present invention results in compressed data that can be uncompressed to offer such ECG-waveform data that exhibits clinically useful ECG waveforms.

These and additional objects and advantages of the present invention will be more readily understood after a consideration of the drawings and the detailed description of the preferred embodiment.

DETAILED DESCRIPTION OF THE PREFERRED MANNER OF PRACTICING THE INVENTION

Figure 1:
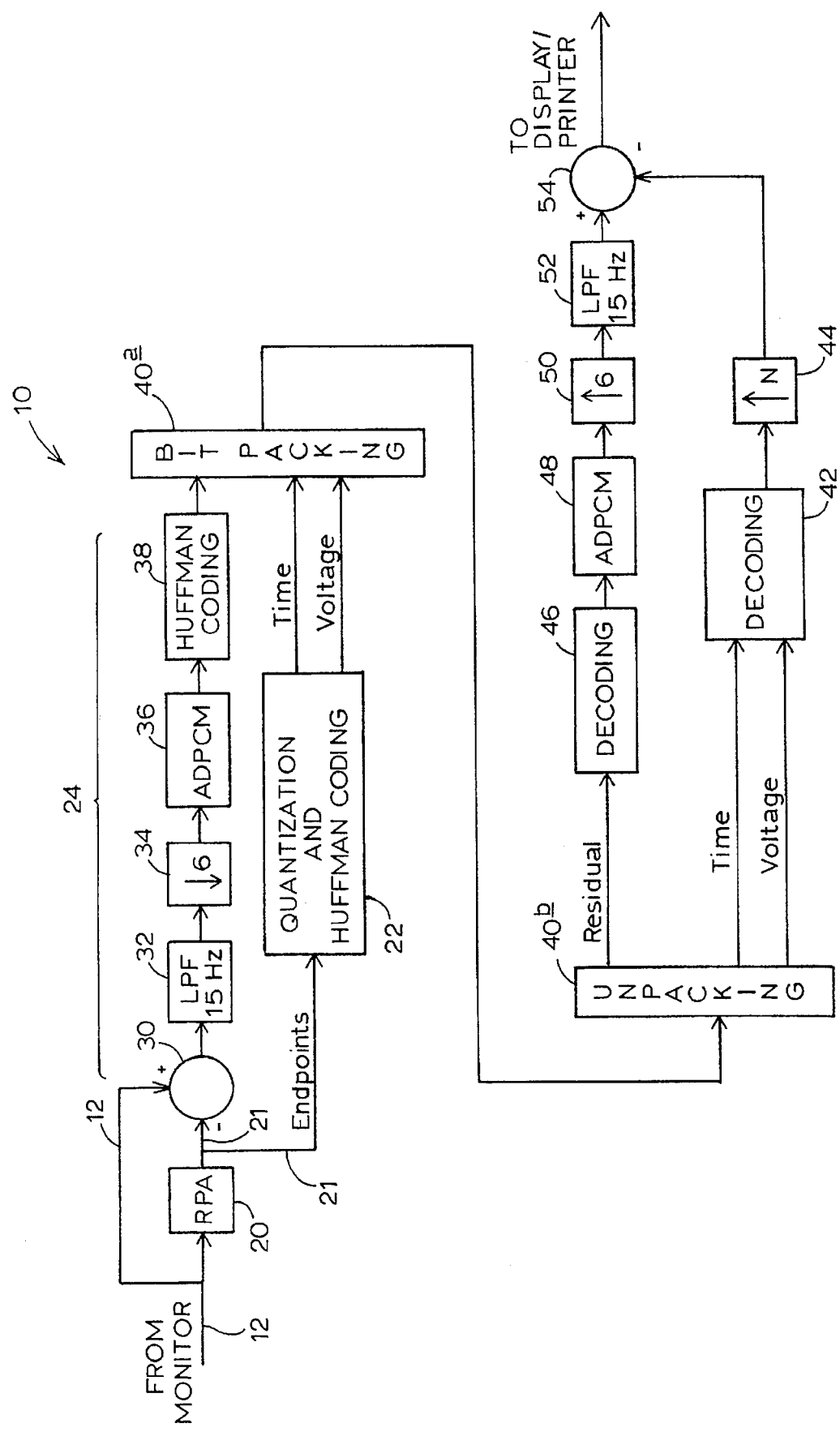
FIG. 1 is a schematic block diagram showing the preferred manner of practicing the present invention.

Turning to the drawings, FIG. 1 shows generally at 10 the steps required to practice the present invention. While the method of the present invention may be practiced on any type of waveform data, it will be described below in connection with ECG-waveform data obtained from an ECG signal generated by a conventional ECG-measuring device.

Preferably, the signal is obtained by using the ACUITY® vital-signs monitoring system which is marketed by Protocol Systems, Inc. That system includes plural, remote vital signs monitors (each with an ECG-measuring capability) which are operatively connected to patients in their hospital rooms and also connected to a central station computer which is capable of receiving the ECG signals from each remote monitor and storing that data. The present invention offers a novel method of compressing ECG-waveform data that is received from such remote monitors.

Also from an overview standpoint, it should be understood that what is being depicted focuses only on certain, to-be-defined steps that are performable by writing a suitable computer program for carrying out such steps. Such program would then be suitably loaded into an electronic vital signs monitoring device such as the PROPAQ® monitor also sold by Protocol Systems, Inc. The PROPAQ® monitor has suitable, conventional ECG equipment for monitoring a living subject's heartbeat. The program that is written based on the present description would be used to direct a microprocessor in the controls of the monitor to function according to desired commands.

As a final overview point, it should be understood that the present invention does not pertain to structure for measuring ECG signals. Rather, the present invention pertains to a method for compressing a signal like an ECG signal which includes waveform data. Therefore the starting point for describing the method is shown in FIG. 1 as an ECG signal, indicated at 12 which is obtainable using desired conventional means such as those described above.

Referring to FIG. 1, the method of the present invention includes examining ECG signal, and then doing various, to-be-defined actions to it as a way of compressing waveform data that it carries. The general idea is that the signal is examined during the periodic occurrence of a heartbeat-induced ECG signal. Such examining step is depicted in FIG. 1 by simply showing ECG signal 12, which signal is received and examined by a suitable monitor, and which signal includes waveform data to be processed as will be described.

Figure 2:
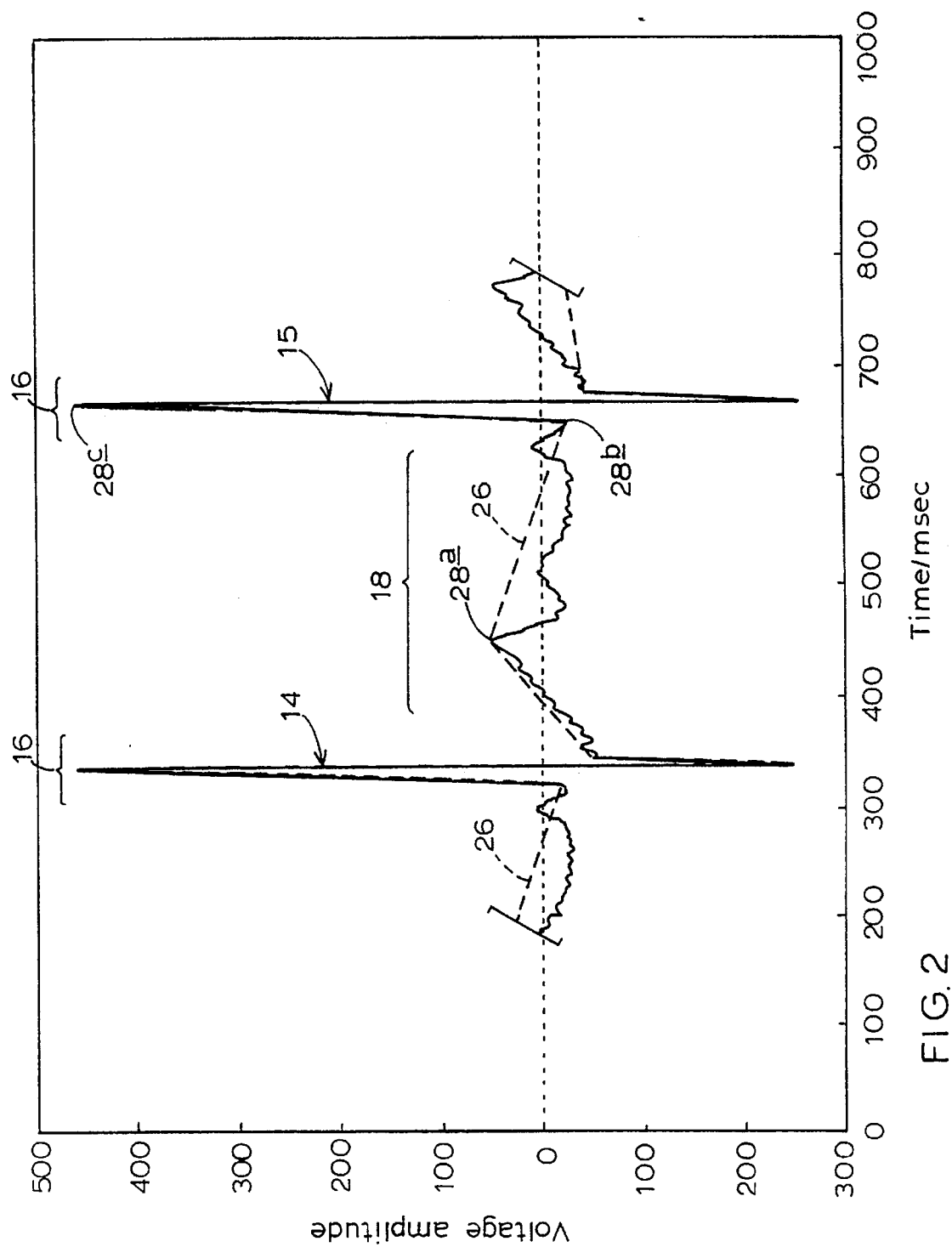
FIG. 2 is a fragmentary plot of ECG-waveform data showing measured data in solid lines with a first region of the data in dashed lines, which region is dominated by to-be-removed, high-frequency information.

Referring for a moment to FIG. 2, certain characteristics of the ECG-waveform data will be described to aid the reader in understanding additional steps of the invention. FIG. 2 shows representative ECG-waveform data with two representative, so-called QRS complexes 14, 15. The ECG-waveform data includes a first region, such as that under bracket 16 which is dominated by high-frequency information and a second region, such as that shown under bracket 18 which is dominated by low-frequency information. The high-frequency information essentially includes QRS complexes (also referred to herein as peaks), like complexes 14,15.

As shown in FIG. 2, there are of course plural ECG waveforms generated by signal 12 (FIG. 1) so it should be understood that reference to first region 16 is meant to include plural QRS complexes and reference to second region 18 is meant to include plural groups of low-frequency information between such complexes.

Referring back to FIG. 1, the reader should now be able to follow a general description of the method of the present invention by retaining the visual handle provided by FIG. 2. Basically, ECG signal 12 is processed along two-tracks and the tracks are formed by performing a removing step, indicated at box 20, which removes or isolates first region 16 (FIG. 2) from the waveform data using what is known as a recursive partitioning algorithm (RPA). RPA 20 will be further described but for now the reader should understand that the RPA provides preselected criteria that are independent of indicia related to first region 16 (FIG. 2). In other words, use of RPA 20 to remove first region 16 from the waveform data does not require the usual beat detector (or other means of reference to prior beat information) that is required by many conventional waveform-compression methods.

Continuing with the description of FIG. 1, processing of ECG signal 12 follows two tracks because the signal is sent both to and around RPA 20. Signal 12 passes through RPA 20 and exits as removed information 21 which relates to removed first region 16 of FIG. 2. Removed information 21 (in the form of to-be-described endpoints) is directed to a to-be-described processing block 22 for processing according to first preselected plan. The ECG signal that is sent around RPA 20 is processed according to a to-be-described second preselected plan indicated generally under bracket 24.

Before focusing on the details of the first and second plans for processing waveform data, RPA 20 will now be further described. To remove or isolate high-frequency information like first region 16 (FIG. 2), ECG signal 12 is buffered and run through RPA 20. As known to those skilled in the art, RPA 20 interpolates a line between the two end points of the buffered data. That interpolated line is then "broken" at the data point which is farthest away from the interpolated line.

The RPA is recursively applied to the two resulting line segments until the maximum error between the data and the linear interpolation is less than a preselected threshold. That presently preferred threshold is chosen to capture QRS complexes (like complexes 14, 15 of FIG. 2) characterized by having a minimum amplitude of 200 μv. The 200-μv threshold is in accord with standards set by the Association for the Advancement of Medical Instrumentation (AAMI). For some applications, even higher compression is obtained by removing extra endpoints in QRS complexes heuristically after running the RPA.

To obtain a further visual handle of what happens to the ECG-waveform data by running the RPA, reference is made again to FIG. 2. FIG. 2 shows a series of dashed line segments 26 which are drawn between endpoints such as 28a, b. It should be understood that each endpoint can be represented by a time/voltage pair, and that using the above-referenced first preselected plan at processing block 22 of FIG. 1, such pairs corresponding to the removed first region are compressed.

Still referring to processing block 22 of FIG. 1, the first-preselected plan will now be described. The plan emphasizes low-bit-rate compression of data from the removed first region for several reasons. First, it involves the use of RPA-removed data which are extremely low-bit-rate since only endpoints (e.g. endpoints 28a, b) are used to represent all data occurring between the endpoints. Second, the plan requires differencing the time values for each pair and then encoding each differenced value using a variable-length entropy code known to those skilled in the art as a Huffman code. The voltage values are compressed with a conventional μ-law characteristic, and uniformly quantized to 6-bit values.

Referring again to the removing step performed by RPA 20, that step also preferably includes the substeps of identifying a potential first region, and confirming that the potential first region is the desired one by using a preselected frequency analysis. To perform these substeps, a potential first region like region 16 of FIG. 2 is identified, and it is presently confirmed by checking that the region is over an empirically derived 15-Hz frequency threshold. If the potential first region does not meet this threshold, then that portion of signal 12 is not captured by RPA 20.

Finally, referring to FIG. 1, second waveform-data-processing plan 24 will now be described. First, removed information 21 generated from the removal step indicated at RPA 20 is subtracted from waveform data carried by signal 12 at summing block 30. The action performed at summing block 30 isolates low-frequency region 18 (FIG. 2). It has been determined empirically that optimally high-quality compression occurs when the low-frequency signal is low-pass filtered at 15 Hz as shown schematically by box 32.

Next, the signal is decimated by a factor of 6 as shown schematically by box 34. With respect to the drawings, decimation operation is indicated by the usual downward pointing arrow, and to-be-described interpolation operation is indicated by the upward pointing arrow. Because conventional, monitor-quality ECG signals have a sampling frequency of about 180-Hz, sampling rate is about 30-Hz after the decimation operation. With respect to the decimation operation, a key point is that the post-decimation, 30-Hz-sampling rate is presently the target rate based on empirical and theoretical information. Therefore, whatever value the monitor-quality ECG-sampling frequency is, it should be decimated to achieve the 30-Hz target rate.

Still referring to FIG. 1, it has been found that applying a backward-adaptive differential pulse code modulator known to those skilled in the art and commonly referred to as a b-ADPCM or simply an ADPCM system is further effective to promote high-quality compression by minimizing the remaining correlation in the low-frequency region. Application of the APDCM system is indicated schematically by box 36. Finally, as described in connection with the first preselected plan, the ECG signal that has been processed via summing block 30, low-pass filter 32, decimation step 34 and ADPCM system 36 is Huffman encoded as indicated schematically by box 38.

Still referring to FIG. 1, the compressed data stream produced according to first processing plan (box 22) and second processing plan (under bracket 24) are bit-packed using known methods with such bit-packing being indicated schematically at box 40a.

The remaining section of FIG. 1 will be only summarily described because it will be apparent to those skilled in the art that uncompressing the data is simply the inverse of the compression process. The data are unpacked (schematically indicated at box 40b) using known methods, and the time/voltage endpoints corresponding to removed information 21 are decoded as indicated schematically at box 42. Next, line segments (e.g. segments 26 of FIG. 2) are interpolated from the endpoints as indicated schematically at box 44. Those skilled in the art will appreciate that box 44 indicates interpolation by the variable N because such interpolation depends on the ΔT corresponding to two given endpoints.

In other words, by referring back to FIG. 2 the reader will appreciate that the aT for endpoints 28a,b will differ from the ΔT corresponding to endpoints 28b,c. Such interpolation methods are well known and it is sufficient for the reader to appreciate the need for interpolation by variable N due to variance in the ΔT corresponding to different pairs of endpoints.

Continuing with the summary description of the uncompressing scheme, the residual (i.e. low-frequency region 18 of FIG. 2) is also decoded, first from its Huffman representation (box 46), and then from its ADPCM representation (box 48), to yield the decimated residual. That residual is then interpolated to the desired output sampling rate (box 50), and low-pass filtered (box 52) to remove spectral images caused by interpolation. The presently preferred sampling rate is about 180-Hz, however any desired rate can be achieved by appropriate interpolation.

After a conventional aligning of the interpolated residual with the interpolated line segments (undepicted but known to those skilled in the art because such delays are inherent in filtering operations), the residual is added to the line segments (generated at box 44) as shown schematically at summing block 54 to complete the uncompressing scheme. The uncompressed waveform data is now in a condition for use/evaluation by a conventional ECG monitor.

Following the above-described waveform-compression method, average bit rates have been obtained as low as about 150–200 bits/sec, thus offering increased waveform-data storage efficiency. Also, waveforms that are uncompressed after being compressed according to the above-described method retain a desired, useful clinical appearance. The above method also effects waveform-data-compression without requiring beat detection. The compressed waveform data also provides increased effective-transmission-bandwidth, which accommodates bidirectional sending of such data using conventional communication systems in vital-signs/ECG monitors.

In addition, due to the high-quality, low-bit-rate compression obtained by practicing the present invention, the method is especially suitable for use with data-archiving applications where full-disclosure archiving of a patient's ECG-waveform data is desired.

While the present invention has been shown and described with reference to the foregoing preferred embodiment, it will be apparent to those skilled in the art that other changes in form and detail may be made therein without departing from the spirit and scope of the invention as defined in the appended claims.

I claim:

1. A high-quality, low-bit-rate method of compressing waveform data obtained from a signal which provides such data in sequences corresponding to periodic events in which such data occurs, comprising:

examining such signal during one such periodic event in which such data occurs, and which data includes a first region dominated by high-frequency information and a second region dominated by low-frequency information;

removing the first region from the event based upon preselected removal criteria, which criteria are independent of a time reference to prior data provided by the signal, wherein the removing step includes the substeps of identifying a potential first region, and confirming that the potential first region is the desired one by using a preselected frequency analysis; and compressing the data by processing the removed first region according to a first preselected plan which emphasizes low-bit-rate compression, and by processing the data of the entire event after the first region has been removed, according to a second preselected plan which emphasizes high-quality compression.

2. The method of claim 1 wherein the examining step involves performing an examination of plural peaks associated with the first region, and the removing step involves using preselected voltage threshold criteria which are independent of relative voltage values of peaks.

3. A high-quality, low-bit-rate method of compressing physiological-waveform data obtained from a signal sent from a diagnostic medical device, which signal provides such data in sequences corresponding to periodic events in which such data occurs, and which signal has time and voltage characteristics associated with it, comprising:

examining such signal during one such periodic event in which such data occurs, and which data includes a first region dominated by high-frequency information and a second region dominated by low-frequency information;

removing the first region from the event based upon preselected removal criteria, which criteria are independent of a time reference to prior data provided by the signal, wherein the removing step includes the substeps of identifying a potential first region, and confirming that the potential first region is the desired one by using a preselected frequency analysis; and compressing the data by processing the removed first region according to a first preselected plan which emphasizes low-bit-rate compression, and by processing the data of the entire event after the first region has been removed, according to a second preselected plan which emphasizes high-quality compression.

4. The method of claim 3 wherein the examining step involves performing an examination of plural peaks associated with the first region, and the removing step involves using preselected voltage threshold criteria which are independent of relative voltage values of peaks.

5. A high-quality, low-bit-rate method of compressing ECG-waveform data obtained from a signal sent from an electronic medical device with ECG-measurement capability, which signal provides such data in sequences corresponding to periodic, heartbeat-induced events in which such data occurs, and which signal has time and voltage characteristics associated with it, comprising:

examining such signal during one such periodic, heartbeat-induced event in which such data occurs, and which data includes a first region dominated by high-frequency information and a second region dominated by low-frequency information; wherein the examining step involves performing an examination of plural peaks associated with the first region, and wherein the removing step involves using preselected voltage threshold criteria which are independent of relative voltage values of peaks removing the first region from the event based upon preselected removal criteria, which criteria are independent of a time reference to prior data provided by the signal, wherein the removing step further includes the substeps of identifying a set of potential plural peaks associated with the first region, and confirming that the potential peaks are the desired ones by using a preselected frequency analysis; and compressing the data by processing the removed first region according to a first preselected plan which emphasizes low-bit-rate compression, and by processing the data of the entire event after the first region has been removed, according to a second preselected plan which emphasizes high-quality compression, with the compressing step resulting in compression of data at the rate of about 150–200 bits/sec.

6. The method of claim 5 wherein the examining step involves performing an examination of plural peaks associated with the first region, and the removing step involves using preselected voltage threshold criteria which are independent of relative voltage values of peaks.

7. A high-quality, low-bit-rate method of compressing waveform data obtained from a signal, and which data includes plural waveforms characterized by having a first region dominated by high-frequency information and a second region dominated by low-frequency information, comprising:

identifying the first region of each waveform;

generating a dataset by using a waveform-data-removal algorithm on the waveform data, wherein data in the dataset corresponds to the first regions of the plural waveform, and wherein the algorithm confirms that an identified first region is a desired one by using a preselected frequency analysis, the algorithm being based upon preselected criteria which are independent of a time reference to prior waveform data in the signal;

making a remainder waveform by removing the dataset from each waveform; and compressing the waveform data by processing the dataset according to a first preselected plan which emphasizes low-bit-rate compression, and by processing the remainder waveform according to a second preselected plan which emphasizes high-quality compression.

8. The method of claim 7 wherein the algorithm is a recursive partitioning algorithm.

* * * * *